United States Patent
Neider

(10) Patent No.: US 9,180,173 B2
(45) Date of Patent: Nov. 10, 2015

(54) METHODS OF TREATING PSORIASIS USING CANDIDA ANTIGEN

(71) Applicant: Stephanie D. Neider, Milton, VT (US)

(72) Inventor: Stephanie D. Neider, Milton, VT (US)

(73) Assignee: Stephanie D. Neider, Milton, VT (US)

( * ) Notice: Subject to any disclaimer, the term of this patent is extended or adjusted under 35 U.S.C. 154(b) by 0 days.

(21) Appl. No.: 14/563,759

(22) Filed: Dec. 8, 2014

(65) Prior Publication Data
US 2015/0157699 A1 Jun. 11, 2015

Related U.S. Application Data

(60) Provisional application No. 61/913,820, filed on Dec. 9, 2013.

(51) Int. Cl.
*A61K 39/00* (2006.01)
*A61K 39/02* (2006.01)

(52) U.S. Cl.
CPC ....... *A61K 39/0002* (2013.01); *A61K 2039/545* (2013.01); *A61K 2039/577* (2013.01)

(58) Field of Classification Search
CPC .............................. A61K 39/02; A61K 39/00
USPC ....................................................... 424/274.1
See application file for complete search history.

(56) References Cited

U.S. PATENT DOCUMENTS

| | | | | |
|---|---|---|---|---|
| 7,629,313 | B2* | 12/2009 | Taylor et al. | 514/1.1 |
| 7,655,248 | B2* | 2/2010 | Clancy et al. | 424/274.1 |
| 2005/0119164 | A1* | 6/2005 | Taylor et al. | 514/8 |
| 2005/0209208 | A1* | 9/2005 | Murase et al. | 514/182 |
| 2007/0041986 | A1* | 2/2007 | Blaszczak et al. | 424/184.1 |
| 2007/0117091 | A1* | 5/2007 | Mahboubi | 435/6 |
| 2007/0275045 | A1* | 11/2007 | Evans et al. | 424/449 |
| 2008/0193481 | A1* | 8/2008 | Bundle et al. | 424/204.1 |
| 2013/0315920 | A1* | 11/2013 | Topp et al. | 424/139.1 |

FOREIGN PATENT DOCUMENTS

WO 03/007953 * 9/2003 ............. A61K 39/02

OTHER PUBLICATIONS

Heriazon, A et al, Veterinary Immunology and Immunopathology, vol. 129, 2009, pp. 93-100, Induction of delayed-type hypersensitivity and interferon-gamma to Candida albicans and anti-hen egg white lysozyme antibody as phenotypic markers of enhanced bovine immune response.*
Tameris, Michele et al, Tuberculosis, Lessons learnt from the first efficacy trial of a new infant tuberculosis vaccine since BCG., vol. 93, 2013, pp. 143-149.*
Corixa, p. 1-4, Feb. 14, 2001, Corixa, Medicis and Genesis announce phase II trial evidence of clinical benefit and safety at 15 microgram dose.*
Dogan, B. et al, International Journal of Dermatology, 1997, vol. 36, pp. 263-265, Intradermal antigen tests and the Koebner phenomenon in psoriasis.*
Ishiguro, A et al, Infection and Immunity, Apr. 1992, vol. 60(4), pp. 1550-1557.*

* cited by examiner

*Primary Examiner* — Albert Navarro
*Assistant Examiner* — Ginny Portner
(74) *Attorney, Agent, or Firm* — Procopio, Cory, Hargreaves & Savitch LLP

(57) ABSTRACT

A method for using a candida antigen in the treatment of psoriasis. In an embodiment, the method comprises periodically administering, to a patient having psoriasis, a candida antigen until clearance of the psoriasis is achieved.

4 Claims, 1 Drawing Sheet

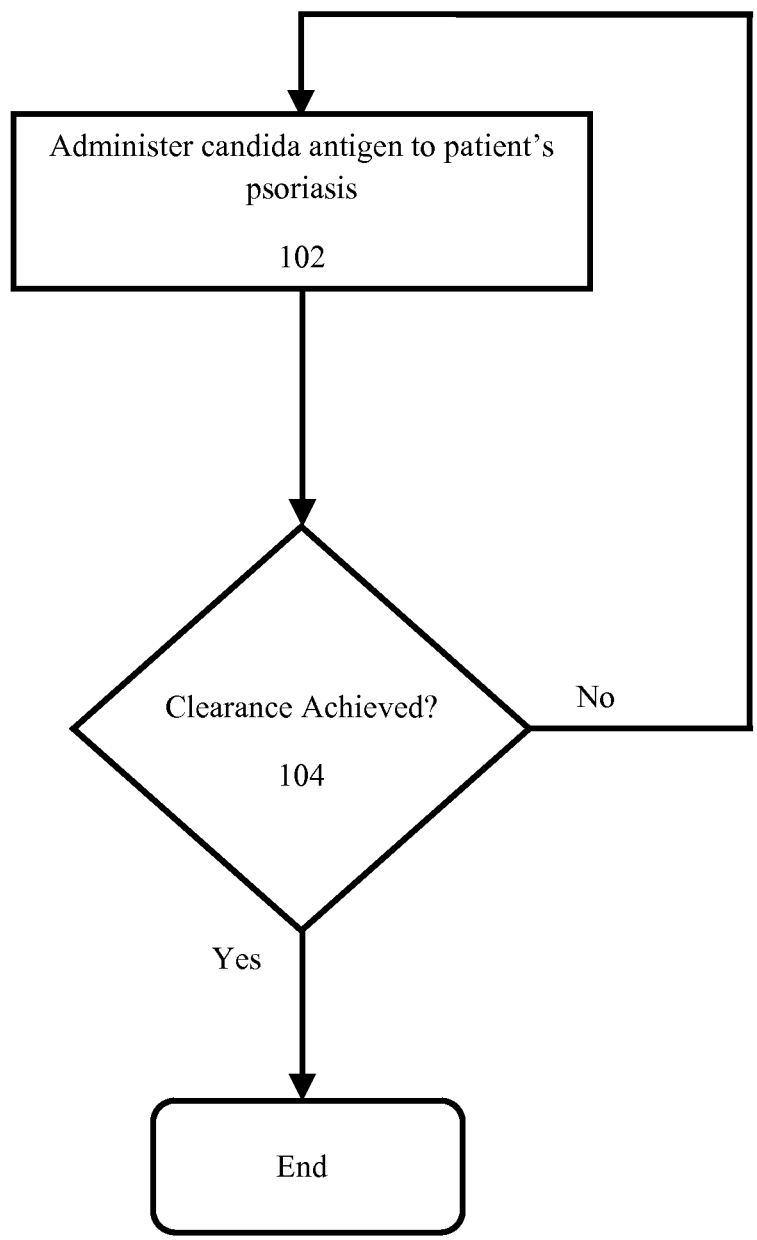

METHODS OF TREATING PSORIASIS USING CANDIDA ANTIGEN

CROSS-REFERENCE TO RELATED APPLICATIONS

This application claims priority to U.S. Provisional Application No. 61/913,820, filed on Dec. 9, 2013, the entirety of which is hereby incorporated herein by reference.

BACKGROUND

1. Field of the Invention

The embodiments described herein are generally directed to the treatment of psoriasis, and, more particularly, to a method or process of using a candida antigen as a treatment for psoriasis.

2. Description of the Related Art

Candida is a genus of yeast that can cause infections. For instance, candida albicans is a species of candida which is commonly known to cause oral and genital infections in humans. Candida yeast is frequently used as the basis of a recall antigen for detecting delayed-type hypersensitivity, through intradermal testing. Specifically, candida antigen has been useful in evaluating the cellular immune response in patients suspected of having a reduced cellular hypersensitivity. For example, when delivered to a patient as a shot, if the patient's immune system is working properly, the skin near the injection site should turn red within a few days. The CANDIN® skin test antigen—manufactured by Allermed Laboratories, Inc. in San Diego, Calif.—is one example of a candida ablicans antigen.

Currently, in the field of dermatology, candida albicans antigens (e.g., CANDIN®) are used to stimulate cellular immune response as a way of treating warts. Warts, which can exist in a number of varieties (e.g., plantar warts), are caused by infections of the human papilloma virus. When the candida antigen is injected into or otherwise delivered to a wart (e.g., plantar wart), a properly functioning human immune system will become very active in the area of the wart. Specifically, the body will attack the candida to remove it, and, in the process, attack the wart as well. In this manner, the wart may be removed through the cellular immune response caused by the delivery of candida antigen to the wart.

Psoriasis is an immune-mediated skin disease. Even today, the cause of psoriasis is not fully understood. Thus, while there are various treatments that can help control the symptoms of psoriasis, there is presently no cure. While candida antigens have been previously used to treat warts, such as plantar warts, it has not been previously contemplated or expected that candida antigens may be useful in the treatment of psoriasis.

SUMMARY

In an embodiment, a method for treating psoriasis is disclosed. The method comprises periodically administering, to a patient having psoriasis, a candida antigen until clearance of the psoriasis is achieved.

In a further embodiment, administering the candida antigen (e.g., a 1:1000 solution of candida albicans antigen, such as CANDIN® or a generic brand of candida antigen) may comprise delivering a dose of the candida antigen to one or more plaques of the psoriasis via an intradermal route. The one or more plaques may comprise a thickest plaque of the psoriasis. In addition, delivering the dose of the candida antigen may comprise injecting the dose into the one or more plaques of the psoriasis. Furthermore, the composition may be administered to the patient every one to four weeks, for example, in 0.1 milliliter doses of CANDIN® or generic candida antigen.

BRIEF DESCRIPTION OF DRAWINGS

Details of the present invention may be gleaned in part by study of the accompanying drawings, in which:

FIG. 1 illustrates a method or process for treating psoriasis using a candida antigen, according to an embodiment.

DETAILED DESCRIPTION

A method or process for treating psoriasis using a candida antigen is disclosed, according to a number of embodiments. The inventor has discovered an unexpected use of the candida antigen as a novel treatment for psoriasis. Specifically, the inventor believes that, at least in some patients, the inflammation of psoriasis may be a hypersensitivity reaction to yeast (e.g., candida albicans). Therefore, desensitizing such patients to yeast (e.g., by treating the patient with a candida antigen) can have beneficial effects in the treatment of their psoriasis.

The inventor initially conceived of a relationship between psoriasis and candida antigens while pondering a particular patient's case. This patient visited the inventor for treatment of both psoriasis and plantar warts. The inventor provided the patient with a steroid cream for the treatment of the psoriasis, and injected the patient with candida antigen for the treatment of the plantar warts.

During a return visit, the inventor discovered that the patient had not utilized the prescribed steroid cream due to a hypersensitivity syndrome that resulted in an intolerance for the cream. Nevertheless, the inventor noticed that the patient's psoriasis had disappeared. Subsequently, the inventor gave the patient a series of shots of candida antigen, spaced four weeks apart, with no other form of therapy. Prior to these shots, the patient suffered from psoriasis covering sixty percent of the surface area of the patient's body. Astoundingly, following the treatment with the candida antigen injections, the patient had no psoriasis.

The inventor also tested candida antigens in the treatment of psoriasis on several other patients. In one case, another patient with both psoriasis and plantar warts was provided with a single candida antigen shot and no separate treatment for the psoriasis. There was a significant reduction in the patient's psoriasis within just four weeks. In fact, all of the inventor's patients who have been treated with the candida antigen have shown significant improvements in their psoriasis.

In an embodiment, this novel treatment of psoriasis comprises delivering a dose of candida antigen (e.g., CANDIN® or generic candida antigen) through an intradermal route (e.g., injection) to the thickest plaque of psoriasis. The dose may comprise 0.1 milliliters of 1:1000 (e.g., 1,000 protein nitrogen units per milliliter (pnu/ml)) CANDIN® skin test antigen or generic candida antigen. For pediatric dosing, the dose may comprise 0.05 milliliters of 1:1000 CANDIN® skin test antigen or generic candida antigen. In addition, the dose may be injected or otherwise delivered periodically, such as every one to four weeks or two to four weeks, until clearance of the psoriasis is achieved. However, it should be understood that other dosages, solutions, antigens, time intervals between dosages, and/or delivery methods are contemplated, and that the combination of these may depend upon the particular case.

FIG. 1 illustrates a method or process of treating psoriasis using a candida antigen, according to an embodiment. In step 102, a candida antigen is administered to the patient's psoriasis. For example, the candida antigen is administered to the thickest plaque of the patient's psoriasis, according to a certain dosage (e.g., a dosage disclosed herein). In step 104, if clearance of the psoriasis has not been achieved, another dosage of candida antigen is administered to the patient's psoriasis. This new dosage may be the same as or different (e.g., weaker or stronger) than a preceding dosage. This process may be continued until clearance of the psoriasis is achieved. It should be understood that clearance of the psoriasis may include both complete clearance (i.e., no psoriasis) or partial clearance (e.g., a reduction in psoriasis) of the patient's psoriasis.

The above description of implementations of the disclosed treatment method is provided to enable any person skilled in the art to make or use the invention. All features of each above-discussed example are not necessarily required in a particular implementation of the disclosed treatment method. In addition, various modifications to these implementations will be readily apparent to those skilled in the art, and the generic principles described herein can be applied to other implementations without departing from the spirit or scope of the invention. Accordingly, additional implementations and variations are also within the scope of the invention. Furthermore, it is to be understood that the present specification is representative of the subject matter which is broadly contemplated by the present invention. The scope of the present invention fully encompasses other implementations that may become obvious to those skilled in the art. Thus, the scope of the present invention is limited by nothing other than the appended claims.

What is claimed is:

1. A method of treating psoriasis, the method comprising every one to four weeks, delivering a therapeutically effective dose of candida antigen to a thickest plaque of psoriasis on a patient, via an intradermal route, until clearance of the psoriasis is achieved, wherein the candida antigen comprises 1,000 protein nitrogen units per milliliter solution of candida albicans extract.

2. The method of claim 1, wherein delivering a therapeutically effective dose of the candida antigen to the thickest plaque of the psoriasis via an intradermal route comprises injecting the therapeutically effective dose into the thickest plaque of the psoriasis.

3. The method of claim 1, wherein the therapeutically effective dose is 0.1 milliliters.

4. The method of claim 1, wherein the therapeutically effective dose is 0.05 milliliters.

\* \* \* \* \*